United States Patent [19]

Iwao

[11] 4,186,295

[45] Jan. 29, 1980

[54] CONTROL SYSTEM FOR A CHROMATOGRAPHY APPARATUS OVEN DOOR

[75] Inventor: Kumiry R. Iwao, Lafayette, Calif.

[73] Assignee: Varian Associates, Inc., Palo Alto, Calif.

[21] Appl. No.: 801,663

[22] Filed: May 31, 1977

Related U.S. Application Data

[63] Continuation of Ser. No. 662,767, Mar. 1, 1976, abandoned.

[51] Int. Cl.$^2$ ............................................ H05B 1/02
[52] U.S. Cl. .................................... 219/497; 219/413; 219/400; 236/15 BR; 126/21 A; 219/510; 73/23.1; 219/498
[58] Field of Search ............... 219/400, 399, 412, 413, 219/494, 497, 510, 498; 13/24; 165/26, 27, 30, 14; 73/23.1; 236/4, 5, 6, 15 BR, 15 BF, 15 A; 432/94; 126/19 R, 21 A

[56] References Cited

U.S. PATENT DOCUMENTS

| | | | |
|---|---|---|---|
| 1,607,054 | 11/1926 | Chadborn | 236/49 |
| 1,952,350 | 3/1934 | Armstrong | 236/49 X |
| 2,698,717 | 1/1955 | Sisco | 236/15 BR |
| 3,305,000 | 2/1967 | Bullen et al. | 165/27 X |
| 3,947,237 | 3/1976 | Leisenberg | 236/15 BR |
| 4,072,846 | 2/1978 | Christer et al. | 219/497 |

OTHER PUBLICATIONS

Computer Control of Gas Chromatographic System-Biler et al.-Hewlett Packard Co.

*Primary Examiner*—Bruce A. Reynolds
*Assistant Examiner*—M. H. Paschall
*Attorney, Agent, or Firm*—Stanley Z. Cole; Gerald M. Fisher; John J. Morrissey

[57] ABSTRACT

In a gas chromatography system of the type including an oven for the GC column, and an electric heater for controllably heating the oven; an improved system is disclosed for controllably opening and closing the oven door to enable a fully controlled heat leak, thereby to stabilize the oven temperature at a desired set point. A signal indicative by first or second conditions of an oven temperature above or below the set point is generated. A heater power control responds to one of the signal conditions by effecting heating of the oven. Bi-directional door motor and actuator means are provided for opening and closing the oven door over a prescribed operating range, and these means are enabled to operate for a predetermined period upon the signal in its first or second condition departing from preset threshold values for a predetermined period whereby closing or opening of the oven door is effected in incremental steps. The door operating range is preferably subdivided, as to define a close-in range proximate to closing, wherein control is effected in reduced sized steps. In consequence, the door may be rapidly brought to the close-in range, whereat the finer control may more effectively bring about the desired stable condition.

5 Claims, 2 Drawing Figures

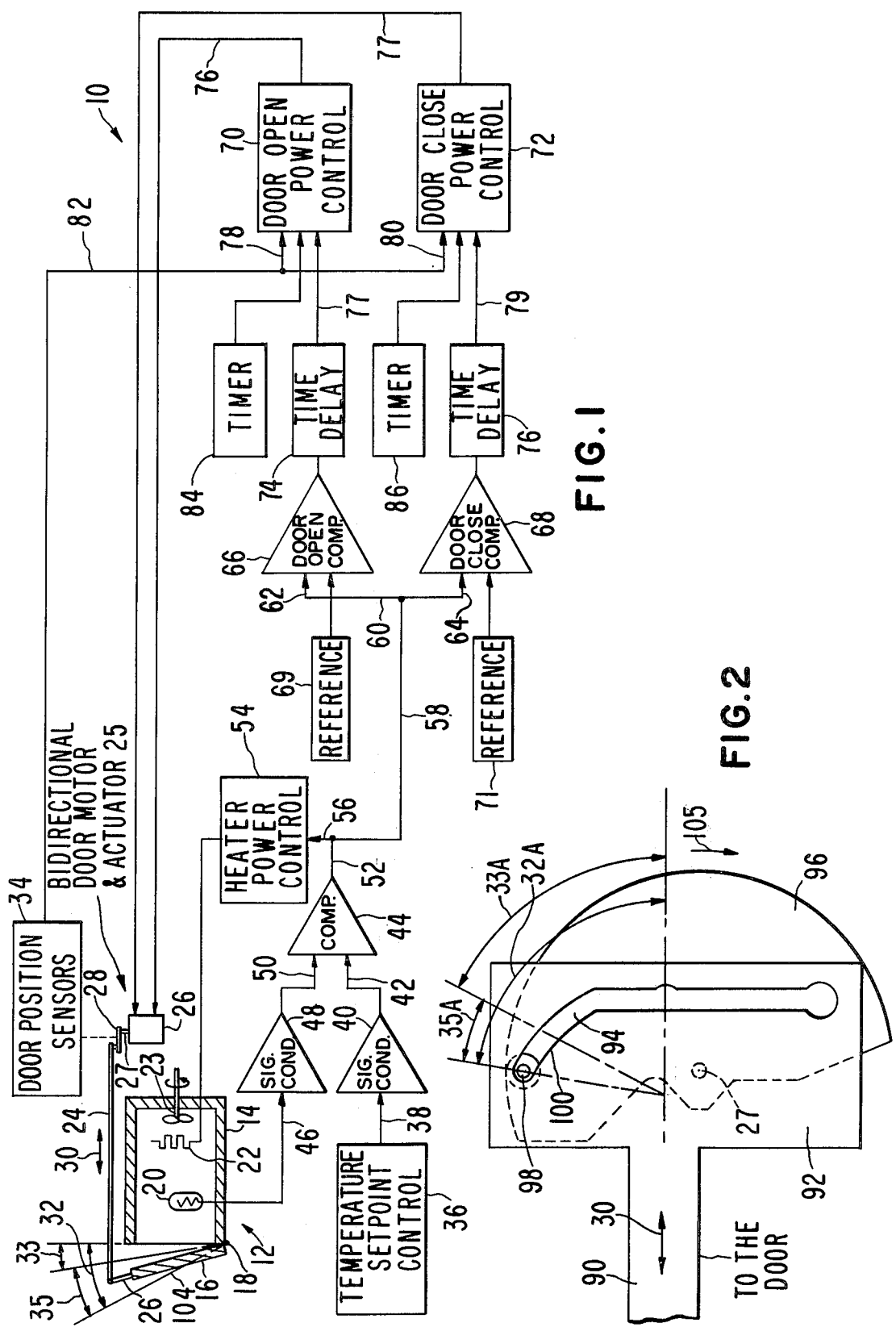

CONTROL SYSTEM FOR A CHROMATOGRAPHY APPARATUS OVEN DOOR

This is a continreation of application Ser. No. 662,767 filed Mar. 1, 1976, abandoned.

BACKGROUND OF INVENTION

This invention relates generally to gas chromatography systems and methodology, and more specifically relates to apparatus and techniques used in such environments for regulating oven temperatures.

Gas chromatographic systems commonly include an oven which surrounds the chromatographic column as to maintain a desired operating temperature. In many instances, an operating temperature range of interest occurs at a zone slightly above ambient. Efforts to maintain the system oven temperature in these ranges, have in the past taken the form on the one hand of overly complex and expensive approaches requiring the use of sophisticated and costly components; or on the other hand relatively makeshift and by and large unacceptable techniques have been utilized.

For example, coolants such as liquid nitrogen or carbon dioxide have been employed where it was necessary to produce temperatures below a minimum level established by heat produced by the oven mixing fan and losses through oven insulation from other heated zones. When desired temperatures were below this minimum level, but higher than ambient air temperature, a common but completely makeshift technique has involved manually opening the oven door to create an uncontrolled heat leak. This last approach, while somewhat effective for its purposes, produces unstable and non-repeatable results.

Within recent years, efforts have been undertaken to mechanize the door opening approach so that the results thereof would be more stable and repeatable in nature. The techniques thus far contemplated, however, have involved simple opening and closing of the said oven door in response to temperature sensor determinations, the net result of which is to produce pulsations of cooler ambient air as the latter enters the oven chamber. In consequence, undesirable gradients can occur. Detectors such as those operating on the thermal conductivity principle, are highly sensitive to such gradients, and the end result is a deterioration of signal quality.

In accordance with the foregoing, it may be regarded as an object of the present invention, to provide a system for controllably opening and closing the oven door in a gas chromatographic system, in such manner that the temperature conditions within the oven may be accurately controlled and rapidly stabilized at a set temperature, without undue oscillations occuring in the said system.

SUMMARY OF INVENTION

In accordance with the present invention, the foregoing object, and others as will become apparent in the course of the ensuing specification, are achieved by means of a control system which utilizes ambient air as the avilable coolant, and applies same continuously and gradually over a broad range according to the power requirement for the oven. A bi-directional door motor and suitable linkage are provided which enable stepwise incremental opening and closing of the oven door over its useful range of operation. A signal generaated by a sensor means positioned in the oven is provided to a comparator, along with an input from the temperature set point control. The comparator enables the heater power control should the sensor indicate a requirement for heating. At the same time, the output from the comparator is provided to a pair of door comparators, which can enable the bi-directional door motor in one or the other of its possible direction of movements, depending upon whether the comparator signal is sufficiently above or below preset reference points. The door comparators are, however, coupled to the door opening and closing power controls which enable the aforementioned motor, through time delay means which inhibit movement of the door unless the temperature deviation from the set point continues for a predetermined period following enablement of the heater power. This arrangement prevents the door controls from reacting to short responses that could be caused by the heater turning on, or by a previous door movement.

Each of the door open and door close power controls are operated for prescribed periods by means of associated timers, so that the door will open or close incrementally. These two times have different periods which are selected so that the door will seek a stable non-oscillating position.

The door operating range is preferably sub-divided, as to define a close-in range proximate to closing, wherein control is effected in reduced sized steps. In consequence, the door may be rapidly brought to the close-in range, whereat the finer control may more effectively bring about the desired stable condition.

BRIEF DESCRIPTION OF DRAWINGS

The invention is diagrammatically illustrated, by way of example, in the drawings appended hereto, in which:

FIG. 1 is a schematic diagram which shows in block form the principal electrical circuitry associated with the present system; the said diagram also schematically illustrates the association of these operative elements with the oven; and FIG. 2 is a plan view of a portion of the actuating mechanism interlinking the bi-directional door motor with the door proper, and illustrates the manner in which a desired modification of the door increments is achieved.

DESCRIPTION OF THE PREFERRED EMBODIMENT

In FIG. 1 a schematic block diagram appears, setting forth in block form the key elements forming part of a control system 10 in accordance with the invention. The control system 10 is shown associated and being utilized with a schematically depicted oven 12. In respect to this embodiment oven 12 includes an enclosure 14 which is accessable by means of an oven door 16, which may be regarded as hinged to enclosure 14 at 18. Oven 12 forms part of a gas chromatographic system, which is otherwise not set forth herein. It should be pointed out, as is known to those skilled in the present art, that the chromatographic column carrying the gaseous elements being analyzed, passes within enclosure 14, where the column and its contents are maintained at an appropriately set temperature. A temperature sensor 20, which may be of conventional design, is mounted in the interior of enclosure 14 for sensing the temperature therein. Similarly, a heater 22 is mounted toward the rear of enclosure 14, and a mixing fan 24 is provided for assuring proper circulation of air within the enclosure, as to enable uniformity of temperature, etc.

In accordance with one aspect of the present invention, opening and closing of door 16 is enabled by a mechanical linkage 24 secured to the door at one end through a link 26. The other end of link 24 is actuated by the bi-directional door motor and actuator means 25. The bi-directional motor 25 may operate through a bell crank actuator 28 which thus may displace link 24 in one or the other of the directions 30 in accordance with the rotational position of the shaft 27 of motor 26. Further aspects of the actuator mechanism will be discussed hereinbelow in connection with FIG. 2.

In the normal course of operation of the present device the door 16 has a useful operating range as is schematically indicated at 32, i.e., a raange within which door 16 is incrementally opened and closed in order to enable the temperature control function of the present device. Door position sensors 34 are provided for establishing information with regard to the position of the door within range 32. These door position sensors may take the form of limit switches, the actuating arms of which may ride upon the periphery face, or on other portions of the crank disc. Protrusions or projections or the like, displace the said arms to indicate desired information about specified door positions including notably the end points of range 32, i.e., they establish a completely "open" position within that range or a completely "closed" position within that operating range.

In accordance with the principles of the present invention, a temperature is initially set by an operator at the temperature set point control 36. The electrical signal proceeding in line 38 from control 36, after being suitably conditioned at conditioner 40, is provided to an input 42 of a comparator 44. The electrical signal from heat sensor 20 within oven 12, is similarly provided by a line 46 to the other input 50 of comparator 44, after first being conditioned at signal conditioner 48.

Comparator 44 provides a signal at its output 52 which may be regarded as of a "positive" or "negative" i.e. displaced to one side or the other of a "zero" condition, these conditions being respectively indicative of a requirement for heating, or indicative of a overheated conditon requiring cooling of oven 12. Assuming for purposes of analysis that the signal is of the "positive" polarity (indicating a heating requirement), the heater power control 54 is enabled via the control line 56, which thus actuates heater 22 to begin heating within the oven.

The signal from comparator 44 is also provided via line 58 to line 60, which in turn has inputs at 62 and 64 to a pair of door comparators, namely a door open comparator 66 and a door close comparator 68. These comparators are respectively associated with a door open power control 70 and a door close power control 72. Actuation of the latter instrumentalities will effect (via lines 76 or 77) operation of door motor 26 in one or the other of its directional modes.

Door comparators 66 and 68 are also provided with inputs from reference signal sources 69 and 71, such inputs being provided to the comparator inputs 71 and 73. These reference levels establish precisely when a signal preceding from comparator 44 is deemed of sufficient magnitude to either close or open the door 16 in the mentioned incremental amount—i.e., use of the threshholds avoids the possibility of the system responding to noise or to such low level changes as could induce system instabilities.

The firstt and second door comparators are seen to be linked with their respective door power controls through time delays 74 and 76. These delays are essentially in the nature of timers, either electronic, mechanical or so forth. Their function is to delay enablement of the associated power control for a prescribed period, in order to prevent the door control from reacting to short responses that could be caused by the heater turning on or by a previous door opening. Only after the mentioned time delay has transpired and the polarity of the signal from comparator 44 remained at its previous polarity (and above the reference threshhold levels) will the time delay cease to inhibit the power controls 70 or 72. At such time enabling signals are provided via lines 77 or 79 to the respective power controls. The door close and door open power controls 70 and 72 are further provided with inputs 78 and 80 which proceed via line 82 from door position sensors 34. These are further enabling inputs for the power controls, in that the incremental closing or opening of door 16 will only be effected if the door condition (as indicated by the sensors) is not such as to "already" be in a fully opened or closed conditon—i.e., at the ends of range 32. If then the enabling signals are provided from both the time delay and the position sensors, the appropriate power control 70 or 72 is actuated for a prescribed period, which will effect an incremental actuation of motor 26, and thus an incremental displacement of door 16 within its operating range 32. The prescribed actuation period is determined by timers 84 or 86, which terminate operation of the associated power control after the period preset in the timer. As has already been mentioned, the periods of timers 84 and 86 are different, and are chosen to assure that the door will always seek a stable, non-oscillating position. Thus, because the times are different, the door can seek an infinite number of positions based on the set point and the ambient temperature.

With the aid of the aforegoing, the operation of the present system in a typical situation may be set forth. In particular it may be assumed that the system operator sets a temperature on control 36 of the order of a few degrees above ambient. Should the sensor 20 indicate that the oven temperature is beneath the set point, heater power control 54 is actuated, which in turn enables heater 22.

The same signal actuating heater control 54 appears as well in line 58, and thus is presented to door comparator 66 and 68. As mentioned, each of these comparators is provided with its own reference level to determine when a signal is of sufficient magnitude to warrant either closing or opening of the door in incremental amounts. Assuming this threshold has been exceeded, an enabling signal is provided to the associated time delay 76. Thus in this instance if heating is still called for after the delay period, a signal will be provided to close door power control 72, and (if the door position is not already fully closed—as determined by the signal in line 82) a signal proceeds through line 76 and will actuate door motor 26 for a period determined by timer 86. This in turn will effect an incremental rotation of shaft 27 to close the door a stepped amount.

The fixed delay provided by time delays 74 and 76 prevents, as mentioned, the door control from reacting to short responses that could in the present instance be caused by the heater turning on, or by a previous door movement. If in the present instance heat was no longer needed before the end of the time delay, the door close power control 72 would simply not be enabled.

If the heat condition, i.e. the enablement of heat power control 54, persists after the allowed stabilization, timer 86 will enable another incremental close. This will continue until either the door position sensors 34 recognize a fully closed door, or until the heat request is removed—indicating a stable oven temperature.

In the inverse situation to that just illustrated, i.e., where the oven is overheated, the revese "polarity" (or signal level) is detected at door open comparator 66, and by a sequence of events as just described, the door will be incremented open for the duration established by timer 84. It is significant to again point out here, that timers 84 and 86 are intentionally provided with different timing values, the purpose of which is one of assuring that the door will always seek a stable non-oscillating position.

Although the bi-directional door motor and actuator 26 has been thus far described as incorporating a simple crank mechanism 28, in a preferable embodiment of the present inventiion a technique is utilized which improves the control technique heretofore discussed. The significance of this further development, may be better appreciated by pointing out that although the total control range for door 16 may include the displacement distance 32, the most effective and, so to speak, "fine control" portion of this range resides close to the position at which the oven door makes contact with enclosure 14, or with the sealing gaskets at such enclosure. This close-in range may be regarded as encompassed within the schematically indicated angle 33. In practice, it is desirable to increment the door by comparatively small steps within this close-in range 33, although within the more distant part of the operating range, i.e., within the range 35, a sequence of relatively "large" steps is perfectly suitable.

In accordance then with this further aspect of the invention, a mechanical linkage arrangement as illustrated in the plan view of FIG. 2 may be utilized to achieve the desired result. In this arrangement, the linkage 24 which effects direct movement of the door 16 may be regarded as embodied within a link 90, i.e., the door moves in directions 30 in accordance with the movement of link 90 in one or the other of the said directions. Link 90, in turn, is secured to a yoke plate 92. The latter is provided with a pin receiving slot 94 so that plate 92 essentially serves as a cam follower. A pin carrying disc 96 underlies plate 92 and is driven about axis 27 by the bi-directional door motor 26. Disc 96 carries a cam pin 98 toward its periphery. This pin passes through slot 94, and during rotation of disc 96, the yoke plate 92 will move in the direction of arrows 30 in accordance with the pin position. The slot 94 carries an appropriate curvature toward its upper end 100 as to assure (in conjunction with the rotation of disc 96), that the desired movement characteristics for opening and closing of door 16 are enabled. The respectively shown positions, i.e., in FIG. 2, of the yoke plate 92 and disc 96 are such that the depicted positions correspond to a relatively "fully" open door, i.e., a door which is at approximately the line 104 defining the most open portion of range 32. It will be evident from consideration of the interaction between pin 98 and slot 94, that as the disc rotates in direction 105, relatively large incremental movements of the door will initially occur, i.e., large increments for each successive equal angular displacement of disc 92 about its axis 27. But, it will similarly be clear that as the progressive rotation of the disc in direction 105 continues, the door increments corresponding to successive angular increments will decrease to smaller steps, i.e., such smaller steps occuring within the range 33 of the overall operating range 32.

It should be noted that FIG. 2 is marked withh rotational displacement angles 32A, 33A, and 35A which correspond to the ranges 32, 33 and 35 in FIG. 1. Particularly to be noted is the very large rotational displacement angle 33 A, which corresponds to the relatively small close-in range 33 in FIG. 1. From this comparison it will be evident how the present arrangement serves to define sub-ranges 35 and 33 within the broader range 32, wherein the effects on the door opening producing by a given angular rotation of disc 96 are relatively amplified or reduced.

While the present invention has been particularly set forth in terms of specific embodiments thereof, it will be understood in view of the instant disclosure, that numerous variations upon the invention are now enabled to those skilled in the art, which variations yet reside within the scope of the present teaching. Accordingly, the invention is to be broadly construed and limited only by the scope and spirit of the claims now appended hereto.

We claim:

1. In a chromatography apparatus of the type including an oven for a chromatographic column and electric heater means for controllably heating said oven, an improved system for controllably opening and closing the door of said oven to enable stabilization of the temperature in said oven at a desired set point, said improved system comprising:

means for generating a signal indicative of the temperature in said oven with respect to said set point;

heater power control means for receiving said oven temperature indicative signal, said control means being enabled by a first condition of said oven to effect heating of said oven and being inactive in response to a second condition of said oven;

bi-directional motor and actuator means for opening and closing said door over a prescribed operating range;

means for enabling said motor and actuator means to operate for a predetermined period upon said oven temperature indicative signal when said oven is in either of said first and second conditions departing from preset threshold values for predetermined periods, whereby opening and closing of said door can be effected in incremental steps; and means for reducing the size of said incremental steps in a sub-range of said prescribed operating range, said sub-range being adjacent the closed position of said door, whereby the incremental steps in said sub-range can be reduced relative to the steps in the remainder of said operating range, thereby to effect fine control of opening and closing of said door in said sub-range.

2. The system of claim 1 wherein said means for reducing the size of said incremental steps in said sub-range comprises:

a disc mounted for rotation by said motor;

cam pin means rotatable by the rotation of said disc;

means linking said cam pin means to said door, whereby opening and closing of said door can be caused by displacements of said cam pin means;

means for converting successive angular displacements of said cam pin means into linear displacements of said linking means; and means for modifying the displacements of said cam pin means as projected on the direction of movement of said linking means, so as to provide modification of incremental displacements of said linking means to effect fine control of the opening and closing of said door in said sub-range.

3. A system for controllably opening and closing a door in a structure defining an enclosure in order to stablize temperature within said enclosure at a desired set point, said system comprising:
  means for generating a signal indicative of the temperature in said enclosure with respect to said set point;
  heater power control means for receiving said temperature indicative signal, said control means being enabled by a first condition of said enclosure to effect heating of said enclosure and being inactive in response to a second condition of said enclosure;
  bi-directional motor and actuator means for opening and closing said door over a prescribed operating range;
  means for enabling said motor and actuator means to operate for a predetermined period upon said temperature indicative signal when said enclosure is in either of said first and second conditions departing from preset threshold values for predetermined periods, whereby opening and closing of said door can be effected in incremental steps; and
  means for reducing the size of said incremental steps in a sub-range of said prescribed operating range, said sub-range being adjacent the closed position of said door, whereby the incremental steps in said sub-range can be reduced relative to the steps in the remainder of said operating range, thereby to effect fine control of opening and closing of said door in said sub-range.

4. The system of claim 3 wherein said means for reducing the size of said incremental steps in said sub-range comprises:
  a disc mounted for rotation by said motor;
  cam pin means rotatable by the rotation of said disc;
  means linking said cam pin means to said door, whereby opening and closing of said door can be caused by displacements of said cam pin means;
  means for converting successive angular displacements of said cam pin means into linear displacements of said linking means; and
  means for modifying the displacements of said cam pin means as projected on the direction of movement of said linking means, so as to provide modification of incremental displacements of said linking means to effect fine control of the opening and closing of said door in said sub-range.

5. The system of claim 4 wherein the structure defining said enclosure is an oven of a chromatographic apparatus.

* * * * *